United States Patent [19]

Klein et al.

[11] Patent Number: 5,086,069

[45] Date of Patent: Feb. 4, 1992

[54] ANTI-THROMBOTIC PEPTIDE AND PSEUDOPEPTIDE DERIVATIVES

[75] Inventors: Scott I. Klein, Audubon; Bruce F. Molino, Hatfield, both of Pa.

[73] Assignee: Rorer Pharmaceutical Corporation, Ft. Washington, Pa.

[21] Appl. No.: 475,043

[22] Filed: Feb. 5, 1990

[51] Int. Cl.$^5$ ................ A01K 31/195; A01K 31/415; A01K 31/405; C07C 279/00
[52] U.S. Cl. .................................... 514/399; 514/419; 514/562; 514/563; 548/341; 548/495; 560/34; 562/426; 562/439
[58] Field of Search ................ 562/439, 426; 560/34; 514/563, 562, 399, 419; 548/341, 495

[56] References Cited

U.S. PATENT DOCUMENTS

| | | | |
|---|---|---|---|
| 4,105,789 | 8/1978 | Ondetti et al. | 562/439 X |
| 4,379,764 | 4/1983 | Fujii et al. | 560/34 X |
| 4,634,715 | 1/1987 | Greenlee et al. | 560/34 X |
| 4,870,207 | 9/1989 | Umezawa et al. | 562/439 |
| 4,956,504 | 9/1990 | Takeuchi et al. | 562/439 X |

FOREIGN PATENT DOCUMENTS 0144717  8/1984  Japan .................................. 562/439

*Primary Examiner*—Joseph Paul Brust
*Attorney, Agent, or Firm*—Darkes, Paul R.; Martin F. Savitzky

[57] ABSTRACT

Disclosed are novel peptide and pseudopeptide derivatives and pharmaceutical compositions thereof that inhibit platelet aggregation and thrombus formation in mammalian blood.

11 Claims, No Drawings

ANTI-THROMBOTIC PEPTIDE AND PSEUDOPEPTIDE DERIVATIVES

BACKGROUND OF THE INVENTION

1. Field of the Invention

This invention relates to novel compounds having anti-thrombotic activity. More particularly, the invention relates to novel peptide and pseudopeptide derivatives that inhibit platelet aggregation and thrombus formation in mammalian blood thereby being useful in the prevention and treatment of thrombosis associated with certain disease states, such as, myocardial infarction, stroke, peripheral arterial disease and disseminated intravascular coagulation.

Haemostasis, the biochemistry of blood coagulation, is an extremely complex and as yet not completely understood phenomena whereby normal whole blood and body tissue spontaneously arrest bleeding from injured blood vessels. Effective haemostasis requires the combined activity of vascular, platelet and plasma factors as well as a controlling mechanism to prevent excessive clotting. Defects, deficiencies, or excesses of any of these components can lead to hemorrhagic or thrombotic consequences.

Platelet adhesion, spreading and aggregation on extracellular matrices are central events in thrombus formation. These events are mediated by a family of platelet adhesive glycoproteins, i.e., fibrinogen, fibronectin, and von Willebrand factor. Fibrinogen is a co-factor for platelet aggregation, fibronectin supports platelet attachments and spreading reactions, and von Willebrand factor is important in platelet attachment to and spreading on subendothelial matrices. The binding sites for fibrinogen, fibronectin and von Willebrand factor have been located on the platelet membrane glycoprotein complex IIb/IIIa.

Adhesive glycoproteins, like fibrinogen, do not bind with normal resting platelets. However, when a platelet is activated with an agonist such as thrombin or adenosine diphosphate, the platelet changes its shape, perhaps making the GPIIb/IIIa binding site accessible to fibrinogen. The novel molecules described in this invention may block the fibrinogen receptor, thus inhibiting platelet aggregation and subsequent thrombus formation. Pharmaceutical agents and/or compositions possessing such an inhibiting effect may be provided for the prophylaxis and treatment of thrombogenic diseases, such as myocardial infarction, stroke, peripheral arterial disease and disseminated intravascular coagulation.

2. Reported Developments

It has been observed that the presence of Arg-Gly-Asp (RGD) is necessary in fibrinogen, fibronectin and von Willebrand factor for their interaction with the cell surface receptor (Ruoslahti E., Pierschbacher, Cell 1986, 44, 517-18). Two other amino acid sequences also seem to take part in the platelet attachment function of fibrinogen, namely, the Gly-Pro-Arg sequence, and dodecapeptide, His-His-Leu-Gly-Gly-Ala-Lys-Gln-Ala-Gly-Asp-Val, sequence. Synthetic small peptides containing the RGD or dodecapeptide units show activity: they bind to the platelet receptor and competitively inhibit binding of fibrinogen, fibronection and von Willebrand factor as well as inhibiting aggregation of activated platelets (Plow et al. Proc. Natl. Acad. Sci. USA 1985, 82, 8057-61; Ruggeri et al. Proc. Natl. Acad. Sci. USA 1986, 5708-12; Ginsberg, et al. J. Biol. Chem. 1985, 260, 3931-36; and Gartner et al. J. Biol. Chem. 1987, 260, 11,891-94).

The present invention is directed to novel peptide and pseudopeptide derivatives which inhibit platelet aggregation and subsequent thrombus formation.

SUMMARY OF THE INVENTION

The present invention comprises novel peptide and pseudopeptide derivatives of the general formula:

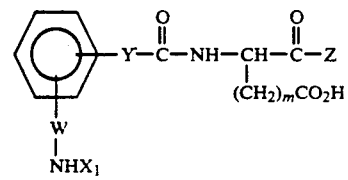

wherein:
Y is —(CH$_2$)$_n$—,
—CH=CH—
—(X—CH$_2$)— or —(CH$_2$—X)—
Z is

—OR$_1$
W is —(CH$_2$)$_n$— or —CH=CH—(CH$_2$)$_p$—
R$_1$ and R$_2$ are independently alkyl, aryl, aralkyl, or allyl;
n is 0 through 6;
m is 1, 2, or 3;
p=0 through 4
X$_1$ is H or amidino; and
pharmaceutically acceptable salts thereof.

DETAILED DESCRIPTION OF THE INVENTION

In accordance with the present invention, novel compounds are provided which inhibit platelet aggregation by inhibiting fibrinogen binding and other adhesive glycoproteins involved in platelet aggregation and blood clotting to activated platelets. Compounds of the present invention, as tested by methods predictive of anti-thrombotic activity, are believed to be useful in the prevention and treatment of thrombosis associated with certain disease states, such as myocardial infarction, stroke, peripheral arterial disease and disseminated intravascular coagulation.

The present compounds may also be useful for the treatment of certain cancerous diseases since they may interfere with adhesive interactions between cancer cells and the extracellular matrix (Journ. of Biol. Chem., Vol. 262, No. 36 1987, pp. 17703-17711; Science, Vol. 233, 1986, pp. 467-470; and Cell, Vol. 57, 59-69, Apr. 1989).

As used herein: alkyl represents a saturated aliphatic hydrocarbon, either branched or straight chained. Preferred alkyl groups contain from about one to about ten carbon atoms, preferably one to six carbon atoms, examples of which include methyl, ethyl, n-propyl, isopropyl, butyl, sec-butyl, t-butyl, amyl and hexyl; aryl preferably denotes phenyl and naphthyl; and aralkyl means an alkyl group substituted by an aryl radical, the preferred aralkyl groups being benzyl and phenethyl. The naturally occuring L-amino acids include:

Val
Ser
Phe
Gly
Leu
Ile
Ala
Tyr
Trp
Thr
Pro
Arg
Asn
Arp
Cyr
Glu
His
Lys and
Met.

The invention also comprises pharmaceutical compositions useful for the prevention and treatment of thrombosis comprising an aforesaid compound in a pharmaceutically acceptable carrier.

Another aspect of this invention comprises a method for the prevention and treatment of thrombosis associated with the aforesaid diseases.

The compounds of the present invention may be readily prepared by standard solid phase or solution phase peptide synthesis techniques using starting materials and/or intermediates available from chemical supply companies such as Aldrich and Sigma or may be synthesized by stardard organic chemical techinques. (H. Paulsen, G. Merz, V. Weichart, "Solid-Phase Synthesis of O-Glycopeptide Sequences", Angew. Chem. Int. Ed. Engl. 27 (1988(; H. Mergler, R. Tanner, J. Gosteli, and P. Grogg, "Peptide Synthesis by a Combination of Solid-Phase and Solution Methods I: A New Very Acid-Labile Anchor Group for the Solid-Phase Synthesis of Fully Protected Fragments". Tetrahedron letters 29, 4005 (1988); Merrifield, R.B., "Solid Phase Synthesis after 25 years: The Design and Synthesis of Antagonists of Glucagon", Makromol. Chem. Macromol. Symp. 19, 31(1988)).

The solid phase method is represented schematically as follows:

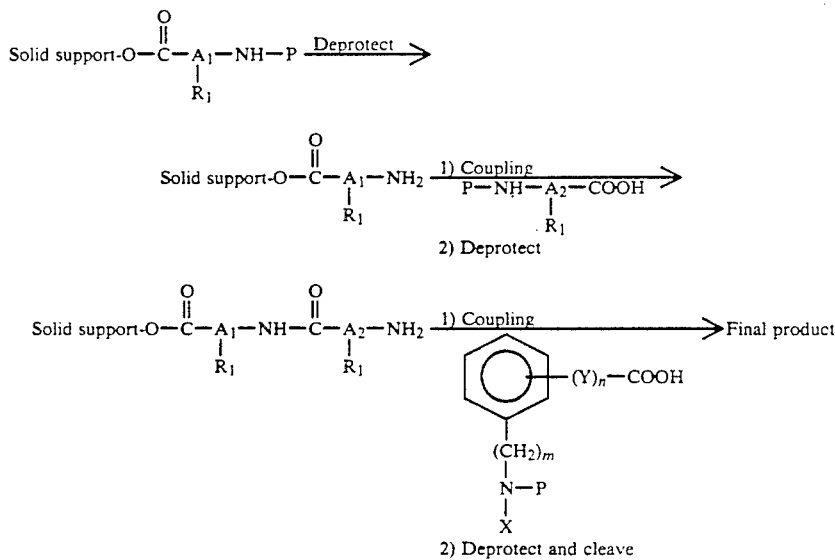

wherein: the solid support may be, but is not limited to, p-alkoxybenzyl alcohol resin;

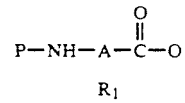

is a protected amino acid derivative;

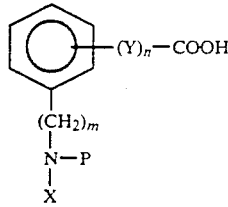

is a protected derivative of an amino or guanidino acid wherein X may be H or amidino, and m and n are independently 0 through 6.

In the process of making the desired compound, the amino acid derivatives are added one at a time to the insoluble resin to give the desired dipeptide resin derivative, then the amino or quanidino acid derivative is coupled to the N-terminal of the chain. Any reactive functional groups of these derivatives are blocked by protecting groups to prevent cross reactions during the coupling procedures. These protecting groups include, but are not limited to, tertiary butoxycarbonyl (BOC), carbobenzoxy (CBZ), benzyl, t-butyl, 9-fluorenylmethoxycarbonyl (FMOC) and methoxy-2,3,6-trimethylbenzenesulfonyl (MTR).

Upon completion of each coupling reaction, the x-amino protecting group is removed by standard procedures and the x-amino group coupled to a derivative having a free carboxylic acid function. The procedure is repeated until the desired product derivative is formed. The final product is obtained by deprotection and cleavage of the product from the resin by standard techniques.

Alternatively, the compounds of the present invention may be prepared in solution, i.e., without using a solid support. In a manner that is similar to the solid phase synthesis, starting with a protected amino acid derivative with a free x-amino group, the protected derivatives are coupled, then deprotected using standard procedures.

The invention will now be explained further by the following illustrative examples:

EXAMPLE 1

N-[3-(2-guanidinoethyl)benzoyl]-L-aspartyl-L-valine

A. A solution of 2.0 g of 3-trifluoromethylphenylacetonitrile in 5 ml of ether was added dropwise to a solution of 0.50 g of lithium aluminum hydride in 20 ml of ether, while cooling at 0° C. The mixture was then stirred at room temperature for four hours and then quenched by sequential addition of 0.5 ml of water, 0.5 ml of 15% sodium hydroxide solution and 1.5 m l of water. The mixture was filtered and the filtrate dried over magnesium sulfate. The filtered solution was acidified with a 1N hydrogen chloride solution in ether and the solid which precipitated was collected to give 2-(3-trifluoromethylphenyl) ethyl amine hydrochloride.

B. 1.38 g of 2-(3-trifluoromethylphenyl) ethyl amine hydrochloride was heated at 100° C. in 3.5 g concentrated sulfuric acid for three hours according to the method of Nikolaus, or disclosed in U.S. Pat. No. 3,792,048, which is incorporated herein by reference. The cooled solution was diluted with 100 ml of ether and the resulting precipitate collected to give 3-(2-aminoethyl)-benzoic acid as the sulfate salt.

C. 1.38 g of the amin salt product from Example 1B was dissolved in 10 ml water and 1N sodium hydroxide solution was added to bring the pH up to 7. The guanidine was then prepared essentially by the method of Miller, et al., *Synthesis*, 777(1986), which is incorporated herein by reference. To the amine solution was added 0.849 g of potassium carbonate, then 0.76 g aminoiminomethanesulfonic acid was added, portionwise, over 10 minutes. The mixture was stirred at room temperature for four hours. Upon reduction of the volume by half, in vacuo, a precipitate formed which was collected and recrystallized from water. The solid was suspended in 20% aqueous tetrahydrofuran. 1N hydrogen chloride in ether was added to give a homogeneous solution which was evaporated in vacuo. The residue was crystallized from methanol/ether to give 3-(2-guanidinoethyl)-benzoic acid hydrochloride.

D. 0.89 g N-(9-fluorenylmethoxycarbonyl)-L-valine-p-alkoxybenzyl alcohol resin ester (containing approximately 0.5 mmol of amino acid) was deprotected by shaking with 10 ml of a solution of 20% piperidine in dimethylformamide for one hour. The mixture was filtered and the resin derivative washed with methylene chloride to give L-valine-p-alkoxy benzyl alcohol resin ester.

E. The product from Example 1D was shaken with 0.822 g N-FMOC-L-aspartic acid-B-t-butyl ester, 0.38 g 1-(3-dimethylaminopropyl)-3-ethylcarbodiimide hydrochloride (EDC), 0.270 g 1-hydroxybenzotriazole (HOBT) and 0.28 ml of triethylamine in 10 ml of dimethylformamide for two hours. The mixture was filtered and the resin derivative washed with methylene chloride. The resin derivative was then deprotected as in Example 1D to give L-aspartyl-β-t-butyl ester-L-L-valine-p-alkoxybenzyl alcohol resin ester.

F. 0.25 g 3-(2-guanidinoethyl)benzoic acid hydrochloride was shaken with the product from Example 1E, 0.191 g EDC, 0.135 g HOBT and 0.14 ml triethylamine in 10 ml of dimethylformamide for two hours. The mixture was filtered and washed with methylene chloride. The β-t-butyl ester blocking group was removed, and the product cleaved from the resin, by treating with 95% trifluoroacetic acid (10 ml) for two hours. The resin was removed by filtration and the filtrate diluted with water, washed with ethyl acetate and lyophilized to give N-[3-2-(guanidinoethyl)benzoyl]-L-aspartyl-L-valine as the trifluoroacetate salt.

EXAMPLE 2

4-(2-quanidinoethyl)benzoyl]-L-aspartyl-L-valine

A. When 4-trifluoromethylphenylacetonitrile was treated in a manner similar to that in Example 1A, 2-(4-trifluoromethyl phenyl) ethyl amine hydrochloride was obtained.

B. When the amine from Example 2A was treated in a manner similar to that in Example 1B, 4-(2-aminoethyl)benzoic acid sulfate was obtained.

C. When the benzoic acid derivative from Example 2B was treated in a manner similar to that in Example 2C, 4-(2-guanidinoethyl)benzoic acid hydrochloride was obtained.

D. 0.272g 4-(2-guanidinoethyl)benzoic acid hydrochloride and L-aspartyl-β-t-butyl ester-L-valine-p-alkoxybenzyl alcohol resin ester (prepared from 1.0 g N-FMOC-L-valine-p-alkoxybenzyl resin ester as in Example 1D,E) were reacted together in the presence of 0.214 g EDC, 0.151 g HOBT, and 0.16 ml triethylamine in 10 ml of dimethylformamide in a manner similar to that of Example 1F. The product was deprotected and cleaved from the resin as in Example 1F to give N-[4-(2-guanidinoethyl)benzoyl]-L-aspartyl-L-valine trifluoroacetate.

EXAMPLE 3

N-(3-guanidinobenzoyl)-L-aspartyl-L-valine

A. 3-guanidinobenzoic acid was prepared from 3-aminobenzoic acid by the method of Miller, et al., cited in Example 1C. The guanidine was treated with ethereal hydrogen chloride to give 3-guanidino-benzoic acid hydrochloride.

B. 3-guanidinobenzoic acid hydrochloride was treated in a manner similar to that in Examples 1F and 2D to give N-(3-guanidinobenzoyl)-L-aspartyl-L-valine.

EXAMPLE 4

N-(4-guanidinomethylbenzoyl)-L-aspartyl-L-valine

A. 4-guanidinomethylbenzoic acid hydrochloride was prepared from 4-aminomethylbenzoic acid in a manner similar to that of Example 3A.

B. 4-guanidinomethylbenzoic acid hydrochloride was treated in a manner similar to that of Examples 1F and 2D to give N-(4-guanidinomethylbenzoyl)-L-aspartyl-L-valine trifluoroacetate.

EXAMPLE 5

N-(3-guanidinomethylbenzoyl)-L-aspartyl-L-valine

A. 3-guanidinomethylbenzoic acid hydrochloride was prepared from 3-aminomethylbenzoic acid in a manner similar to that of Example 3A.
B. 3-guanidinomethylbenzoic acid hydrochloride was treated in a manner similar to that of Examples 1F and 2D to give N-(3-guanidinomethylbenzoyl)-L-aspartyl-L-valine as the trifluoroacetate salt.

EXAMPLE 6

N-(4-quanidinobenzoyl)-L-aspartyl-L-valine

A. 4-guanidinobenzoic acid hydrochloride was prepared from 4-aminobenzoic acid in a manner similar to that of Example 3A.
B. 4-guanidinobenzoic acid hydrochloride was treated in a manner similar to that of Examples 1F and 2D to give N-(4-guanidinobenzoyl)-L-aspartyl-L-valine as the trifluoroacetate salt.

EXAMPLE 7

N-[3-(2-aminoethyl)benzoyl]-L-aspartyl-L-valine

A. One equivalent of 3-(2-aminoethyl)benzoic acid (prepared as in Example 1C) is stirred with one equivalent of di-t-butyl-dicarbonate in the presence of two equivalents of sodium carbonate in tetrahydrofuran/water (1:1). The reaction mixture is evaporated to remove the tetrahydrofuran and the aqueous is acidified with dilute hydrochloric acid. The product is extracted into ethyl acetate and the solution is dried, then evaporated to give N-tert-butoxycarbonyl-3-(2-aminoethyl)benzoic acid.
B. If N-BOC-3-(2-aminoethyl)benzoic acid is substituted for 3-(2-guanidinoethyl)benzoic acid hydrochloride in Example 1F, and treated similarly, then N-[3-(2-aminoethyl)benzoyl]-L-aspartyl-L-valine is obtained as the trifluoroacetate salt.

EXAMPLE 8

N-(4-guanidinophenylacetoyl)-L-aspartyl-L-valine

A. If 4-aminophenylacetic acid is substituted for 3-(2-aminoethyl)benzoic acid in Example 1C, and treated similarly, then 4-guanidinophenylacetic acid hydrochloride is obtained.
B. If 4-guanidinophenylacetic acid hydrochloride is substituted for the benzoic acid in Example 1F and treated similarly, then N-(4-guanidinophenylacetoyl)-L-aspartyl-L-valine is obtained as the trifluoroacetate salt.

EXAMPLE 9

N-(4-aminophenylacetoyl)-L-aspartyl-L-valine

A. If 4-aminophenylacetic acid is substituted for the benzoic acid in Example 7A, and treated similarly, then N-tert-butoxycarbonyl-4-aminophenylacetic acid is obtained.
B. If N-BOC-4-aminophenylacetic acid is substituted for 3-(2-guanidinoethyl)benzoic acid hydrochloride in Example 1F, and treated similarly, then N-(4-amino-phenylacetoyl)-L-aspartyl-L-valine is obtained as the trifluoroacetate salt.

EXAMPLE 10

4-Guanidino cinnamoyl-L-aspartyl-L-valine

In a manner similar to that used in the previous examples, 4-guanidino cinnamoyl-L-aspartyl-L-valine as the trifluoroacetate salt is prepared.

Compounds of the present invention were tested for inhibition of platelet aggregation using the following procedures:

I. Inhibition of Radiolabeled ($^{125}I$) Fibrinogen Binding Assay, which is essentially based on the method described in Proc. Natl. Acad. Sci. USA Vol. 83, pp. 5708-5712, Aug. 1986, and is as follows.

Platelets are washed free of plasma constituents by the albumin density-gradient technique. In each experimental mixture platelets in modified Tyrode's buffer are stimulated with human α-thrombin at 22°-25° C. for 10 minutes ($3.125 \times 10''$ platelets per liter and thrombin at 01 N1H units/ml). Hirudin is then added at a 25-fold excess for 5 minutes before addition of the radiolabeled ligand and any competing ligand. After these additions, the final platelet count in the mixture is $1 \times 10''$/liter. After incubation for an additional 30 minutes at 22°-25° C., bound and free ligand are separated by centrifuging 50 μl of the mixture through 300 μl of 20% sucrose at 12,000 xg for 4 minutes. The platelet pellet is then separated from the rest of the mixture to determine platelet-bound radioactivity. Nonspecific binding is measured in mixtures containing an excess of unlabeled ligand. When binding curves are analyzed by Scatchard analysis, nonspecific binding is derived as a fitted parameter from the binding isotherm by means of a computerized program. To determine the concentration of each inhibitory compound necessary to inhibit 50% of fibrinogen binding to thrombin-stimulated platelets ($IC_{50}$), each compound is tested at 0.176 μgmol/liter (60 μg/ml). The $IC_{50}$ is derived by plotting residual fibrinogen binding against the logarithm of the sample compound's concentration.

II. Inhibition of Fibrinogen—Mediated Platelet Aggregation, which is essentially based on the method described in Blood, Vol. 66, No. 4, Oct. 1985, pp. 846-952, and is as follows.

Human Platelets were isolated from freshly drawn whole blood and were suspended in 0.14 mol/L NaCl, 2.7 mmol/L K11, 12 mmol/L $NaHCO_3$, 0.42 mmol/L $Na_2HPO_4$, 0.55 mmol/L glucose, and 5 mmol/L Hepes, pH 7.35 at $2 \times 10^8$ platelets/ml. The suspension was incubated at 37° C. An aliquot of 0.4 ml of platelet suspension was activated by human thrombin at a final concentration of 2 μg/ml of thrombin for one minute. After one minute the reaction was stopped by a thrombin inhibitor. Serial dilution of the compound being tested was then added to the activated platelet, the reaction was allowed to proceed for one minute, followed by the addition of human fibrinogen at a final concentration of 60 μ/ml of fibrinogen. Platelet aggregation was then recorded by an aggregometer. Rate of aggregation was used to calculate $IC_{50}$.

Representative results of platelet aggregation inhibition are shown in Table I.

TABLE I

| | $IC_{50}$ (μM) | Inhibition of Fibrinogen Mediated Platelet Aggregation | |
|---|---|---|---|
| | | $IC_{50}$ (μM) | % inhibition at 25 μM |
| | Inhibition of $^{125}$I-Fibrinogen | | |
| 3-(2-Guanidinoethyl)-benzoyl-L-aspartyl-L-valine | 115.0 | 33.1 | 37.0 |
| 4-(2-Guanidinoethyl)-benzoyl-L-aspartyl-L-valine | 10.9 | 7.7 | 85.0 |
| 4-Guanidino cinnamoyl-L-aspartyl-L-valine | 0.25 | 2.8 | 25.0 |
| 4-Guanidinomethyl phenylacetoyl-L-aspartyl-L-valine | * | — | 42.0 |
| 3-(4-guanidinophenyl)propanoyl-L-aspartyl-L-valine | 4.5 | 14.0 | 65.0 |
| 4-(3-Guanidinopropyl)benzoyl-L-aspartyl-L-valine | — | 7.6 | 83.3 |
| 4-Guanidinophenylacetoyl-L-aspartyl-L-valine | 20.0 | — | 43.0 |
| 4-Guanidinobenzoyl-L-aspartyl-L-valine | * | — | 33.0 |
| 3-Guanidinomethyl benzoyl-L-aspartyl-L-valine | * | 30.2 | 53.0 |
| 4-Guanidinomethyl benzoyl-L-aspartyl-L-valine | 22.0 | — | 16.0 |
| 3-Guanidinobenzoyl-L-aspartyl-L-valine | * | — | 6.3 |
| | Inhibition of $^{125}$I-Platelet | | |
| 3-Guanidinomethylphenylacetoyl-L-aspartyl-L-valine | — | — | 15.2 |
| 3-(3-Guanidinopropyl)benzoyl-L-aspartyl-L-valine | * | — | 52.0 |

*no inhibition of $^{125}$I - Fibrinogen binding observed at concentrations of 50 μM or lower.

The compounds of the present invention may be orally or parenterally administered to mammals. The compound may be incorporated into pharmaceutical formulations having excipients suitable for these administrations and which do not adversely react with the compounds, for example, water, vegetable oils, certain alcohols and carbohydrates, gelatin and magnesium stearate. The pharmaceutical formulations containing an active compound of the present invention may be made into: tablets, capsules, elixirs, drops or suppositories for enteral administration; and solutions, suspensions or emulsions for parenteral administration.

In general, compound of this invention is administered in dosages of approximately 1 to 200 mg per dosage unit or higher. The daily dosage is approximately 0.02-5 mg/kg of body weight. It is to be understood, however, that the particular dose for each patient as usually depends on very diverse factors, such as the age, body weight, general condition of health, sex diet and the like of the patient, on the time and route of administration, on the rate of excretion, on the combination of medicaments and on the severity of the disease.

Having described the invention, it will be apparent to one of ordinary skill in the art that changes and modifications can be made thereto without departing from the spirit and scope of the invention as set forth herein.

What is claimed is:

1. A compound of the formula

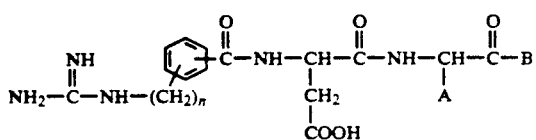

wherein:

A is hydrogen, methyl, isopropyl, benzyl, n-but-2-yl, 2-methylprop-1-yl, hydroxymethyl, 4-hydroxybenzyl, indol-3-ylmethyl, mercaptomethyl, methylthioethyl, carboxymethyl, carbamoylmethyl, 2-carboxyethyl, 2-carbamoylethyl, imidazol-3-ylmethyl, 3-guanidinopropyl, or 4-aminobutyl;

B is —OH or —NH$_2$; and n is 0 to about 6;

or a pharmaceutically acceptable salt thereof.

2. A pharmaceutical composition for the prophylaxis or treatment of abnormal thrombus formation in a mammal comprising a pharmaceutically acceptable carrier and a pharmaceutically effective amount of a compound of claim 1.

3. A method of preventing or treating thrombus formation in a mammal comprising the administration of a pharmaceutically effective amount of the composition of claim 1.

4. N-[3-(2-guanidinoethyl)benzoyl]-L-aspartyl-L-valine or a pharmaceutically acceptable salt thereof.

5. N-(3-guanidinobenzoyl)-L-aspartyl-L-valine or a pharmaceutically acceptable salt thereof.

6. N-(4-guanidinomethylbenzoyl)-L-aspartyl-L-valine or a pharmaceutically acceptable salt thereof.

7. N-(3-guanidinomethylbenzoyl)-L-aspartyl-L-valine or a pharmaceutically acceptable salt thereof.

8. N-(4-guanidinobenzoyl)-L-aspartyl-L-valine or a pharmaceutically acceptable salt thereof.

9. N-(4-(2-guanidinoethyl)benzoyl)-L-aspartyl-L-valine or a pharmaceutically acceptable salt thereof.

10. N-(4-(3-guanidinopropyl)benzoyl)-L-aspartyl-L-valine or a pharmaceutically acceptable salt thereof.

11. N-(3-(3-guanidinopropyl)benzoyl)-L-aspartyl-L-valine or a pharmaceutically acceptable salt thereof.

* * * * *